United States Patent [19]

Elenewski

[11] Patent Number: 5,023,023
[45] Date of Patent: Jun. 11, 1991

[54] METHOD OF FORMING CURVED TRANSPARENT CELLULOSE DIACETATE VISOR HAVING SILK SCREENED ELECTRIC HEATING CONDUCTOR

[76] Inventor: Allen Elenewski, Rte. 2, 2270 15th La., Friendship, Wis. 53934

[21] Appl. No.: 369,407

[22] Filed: Jun. 20, 1989

[51] Int. Cl.⁵ ............................................... B29C 51/14
[52] U.S. Cl. ...................................... 264/1.7; 264/2.7; 264/510; 264/134
[58] Field of Search ................. 264/1.7, 2.7, 510, 512, 264/129, 134; 427/108, 110; 156/102, 99

[56] References Cited

U.S. PATENT DOCUMENTS

| | | |
|---|---|---|
| 2,954,454 | 9/1960 | Gaiser . |
| 3,001,901 | 9/1961 | Barkley ............................... 156/102 |
| 3,041,668 | 7/1962 | Bonza et al. ......................... 264/2.7 |
| 3,832,527 | 8/1974 | Nagasima . |
| 4,063,247 | 12/1977 | Sakurai et al. . |
| 4,137,447 | 1/1979 | Boaz . |
| 4,166,876 | 9/1979 | Chiba et al. ........................ 427/110 |
| 4,170,618 | 10/1979 | Adams ............................... 264/554 |
| 4,196,338 | 4/1980 | Edel . |
| 4,231,827 | 11/1980 | Wilson et al. ....................... 264/2.7 |
| 4,339,400 | 7/1982 | Sorko-Ram ......................... 264/2.7 |
| 4,388,522 | 6/1983 | Boaz . |
| 4,445,953 | 5/1984 | Hawk .................................. 156/102 |
| 4,638,728 | 1/1987 | Elenewski . |
| 4,668,270 | 5/1987 | Ramus . |
| 4,682,007 | 7/1987 | Hollander .......................... 219/211 |

*Primary Examiner*—Jill L. Heitbrink
*Attorney, Agent, or Firm*—Lowe, Price, LeBlanc, Becker & Shur

[57] ABSTRACT

An electric heater is silk screened on an interior surface of a cellulose diacetate visor by applying silk screening ink through a silk screen mask to a flat cellulose diacetate blank. The ink is then dried by being heated to between 120° F.–150° F. for about 20 seconds, preferably by air jet drying. The cellulose diacetate sheet is then formed into visor shape and cured by heating in an oven at about 325° F. for about 20 minutes on a drape and/or vacuum form. The temperature of the visor during the drying, as well as bending and curing stages, is carefully controlled to assure proper application of the ink as well as the mechanical integrity and transparency of the visor.

18 Claims, 3 Drawing Sheets

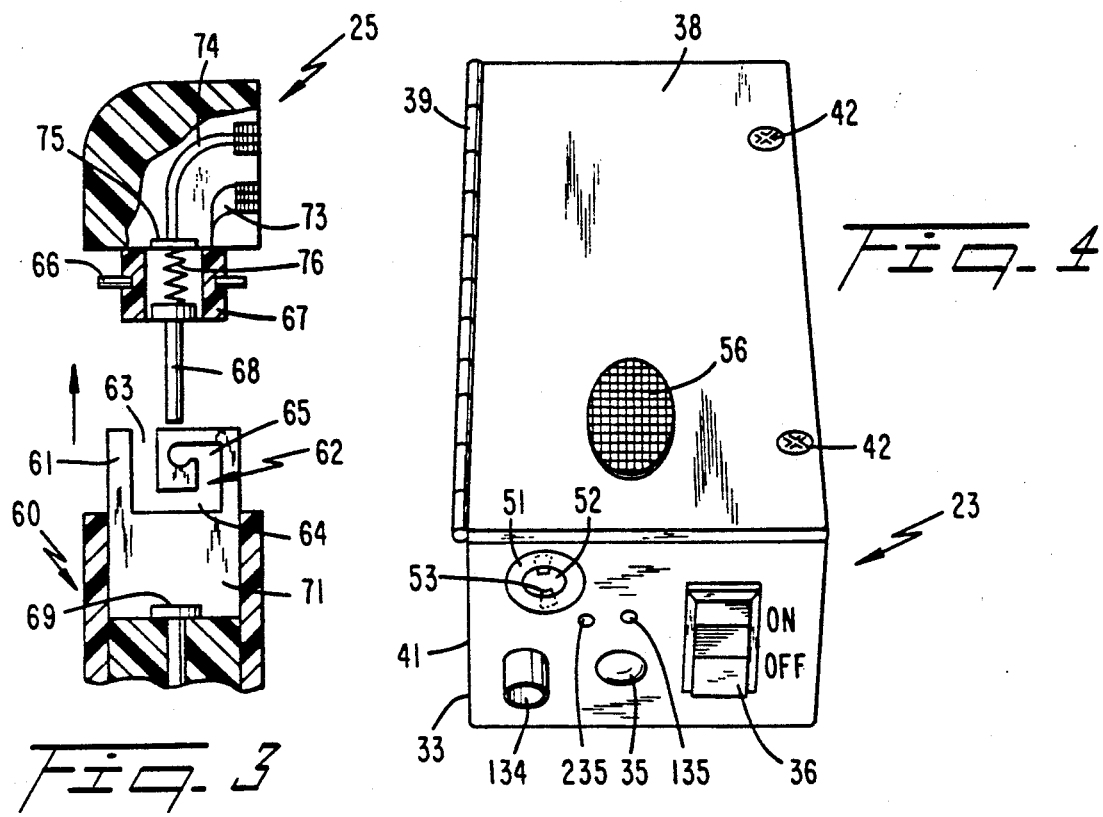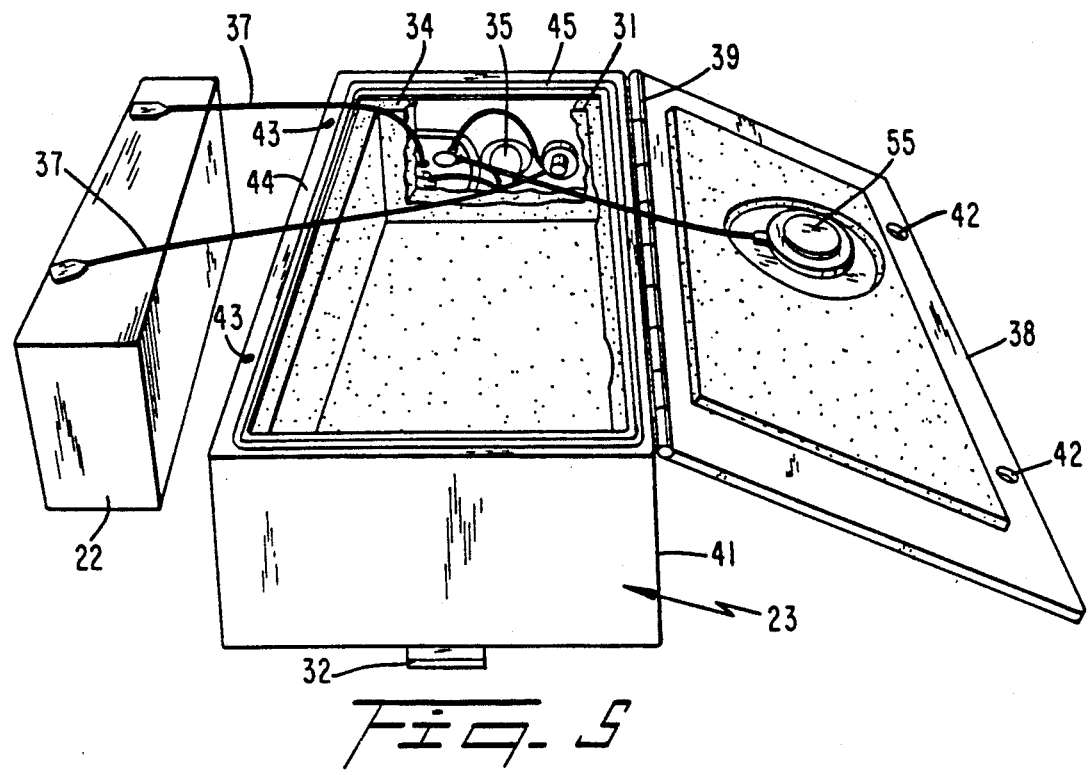

METHOD OF FORMING CURVED TRANSPARENT CELLULOSE DIACETATE VISOR HAVING SILK SCREENED ELECTRIC HEATING CONDUCTOR

TECHNICAL FIELD

The present invention relates generally to methods of forming curved transparent cellulose diacetate visors having electric heating conductors formed thereon and more particularly to silk screening an electric heating conductor onto a cellulose diacetate visor by applying silk screening ink through a silk screen mask to a flat cellulose diacetate blank, then bending the blank about a form with the ink dried thereon while the blank is heated to a plastic state and then curing.

BACKGROUND ART

In my U.S. Pat. No. 4,638,728 there is disclosed a curved Plexiglas visor on which an electrical resistance heating coil is formed to remove and/or prevent condensation of human breath. The coil, while connected to an electric power source, has sufficient current supplied to it to prevent formation of breath condensate on the visor or to remove the condensate. The prior art devices are fabricated by bonding preformed metal films to the interior surface of the curved Plexiglas visors, i.e., to the surface having the greatest curvature, or by painting or pad printing a layer of copper covered by a silver layer on the curved interior surface. While the prior art devices perform satisfactorily to remove and/or prevent the formation of vapor, the methods of applying the coil are relatively expensive.

Therefore, an object of the invention is to provide a new and improved method of applying an electric conducting film to a cellulose diacetate shield that eventually is curved into the shape of a visor.

Yet an additional object of the invention is to provide a method of silk screening a metal film onto a cellulose diacetate sheet that is bent to form.

DISCLOSURE OF THE INVENTION

In accordance with the present invention the electric conducting coil is silk screened to a cellulose diacetate visor by a method which enables the visor to retain its optically transparent properties. Silk screening ink is applied through a silk screen mask to a flat cellulose diacetate blank. The ink is then dried, preferably by air jet drying at about 120° F. for about 20 seconds. The cellulose diacetate sheet is then formed into visor shape and cured by heating in an oven at about 325° F. for about 20 minutes on a drape and/or vacuum form. The temperature of the visor during the drying, as well as bending and curing stages, must be carefully controlled to assure proper application of the ink as well as the mechanical integrity and transparency of the visor.

The present invention can be used for visors used with open air outdoor vehicles, as disclosed in my previously mentioned patent, or with self-contained breathing apparatus (SCBA), as disclosed herein.

BRIEF DESCRIPTION OF DRAWINGS

FIG. 3 is a side sectional view of the connector parts illustrated in FIG. 2;

FIG. 4 is a perspective view of a housing for a battery adapted to be utilized with the combination of FIG. 1;

FIG. 5 is a view of the interior of the battery housing illustrated in FIG. 4;

DESCRIPTION OF THE PREFERRED EMBODIMENTS

Figure 1:
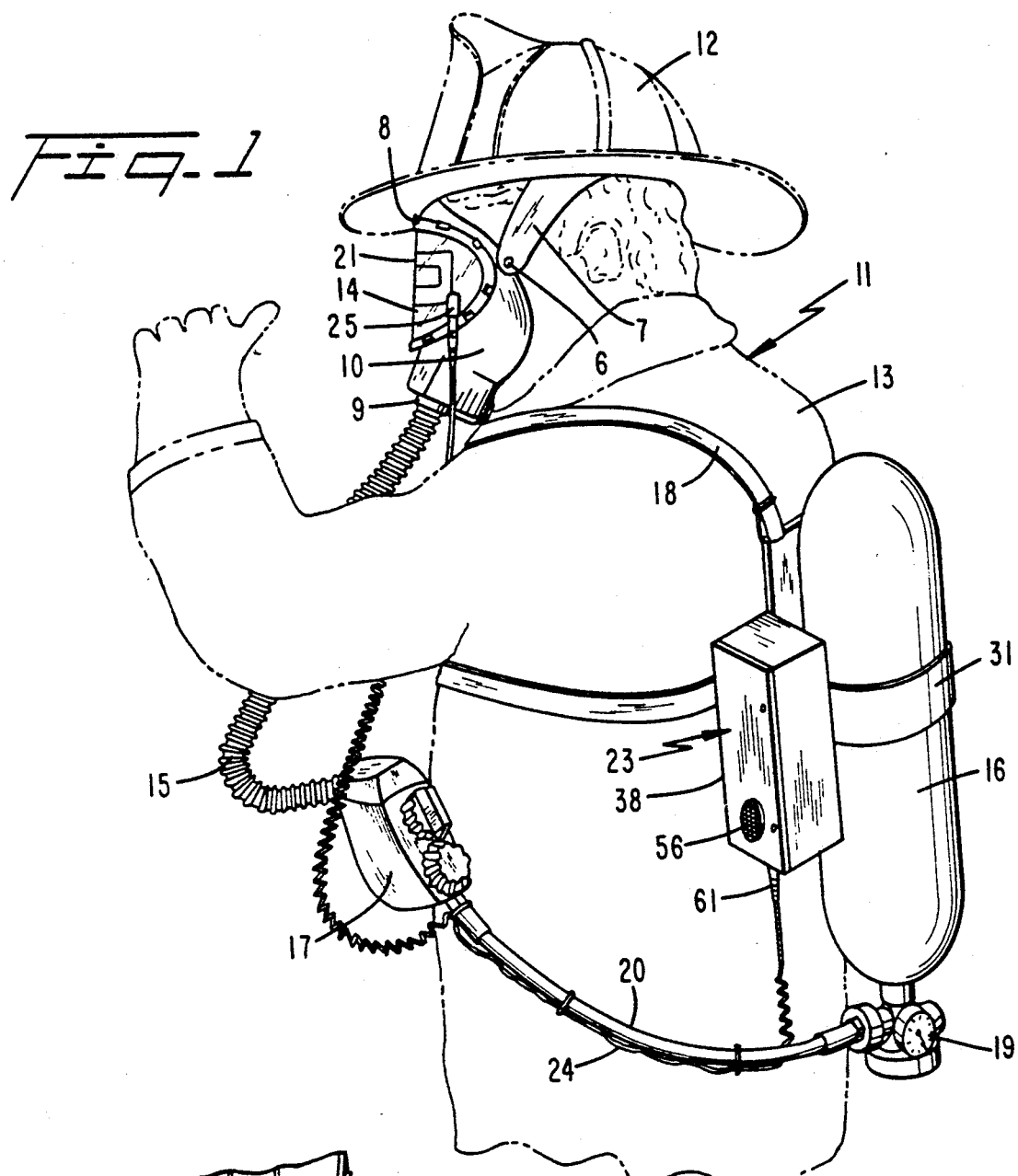
FIG. 1 is an illustration of a firefighter equipped with an SCBA including an electrically activated heating device for removing and/or preventing visor condensate in accordance with one embodiment of the present invention.

Reference is now made to FIG. 1 wherein firefighter 11 is illustrated as wearing a conventional metal hard hat 12, fire protection coat 13 and self contained breathing apparatus (SCBA). The SCBA includes a face mask containing rubber like shell 10 that is in sealing relation around the periphery of the face of firefighter 11. On face shield 10 is mounted optically transparent, visor 14 preferably formed of the organic compound, cellulose diacetate, that is located in front of the eyes and nose of firefighter 11. Visor 14 is secured to face shield 10 by snaps 8 to facilitate removal of the visor from the face shield. Strap 7 holds face shield 10 securely in place on the face of firefighter 11 so the periphery of the face shield abuts against the facial skin of the firefighter to form a gas seal for his nose and mouth. Strap 7 is connected by fastener 6 to opposite exterior portions of face shield 10 at the same level as the ear of the firefighter 11. Strap 7 extends about the top of the head of the firefighter.

Face shield 10 includes aperture or orifice 9 into which hose 15 is fitted in sealing relation. Hose 15 extends to compressed air metal tank 16 by way of regulator 17, line 20 and valve 19. Tank 16 is mounted on the back of firefighter 11 by harness 18. Initially, tank 16 typically has enough compressed air therein to enable firefighter 11 to work for about 10 to 15 minutes in an environment of noxious fumes as frequently exists in fires in modern structures. The foregoing structure is well-known to those skilled in the art of modern fire fighting techniques.

A problem with the foregoing, prior art structure is that the interior and exterior surfaces of visor 14 have a tendency to become fogged, resulting in the vision of firefighter 11 becoming obscured when attempting to look through transparent visor 14. The interior face of visor 14, i.e., the face of the visor closest to the face of firefighter 11, becomes fogged as a result of perspiration from the face of the firefighter vaporizing and condensing on it. The exterior face of visor 14 becomes fogged when excessive water vapor, e.g., steam, in the region where firefighter 11 is located. Excessive water vapor occurs in the region for various reasons, e.g., in response to high pressure water from the firefighter's hose being incident on a hot, burning object. The steam from the object condenses on the exterior face of visor 14.

The fogging problem is such that firefighters frequently must leave a burning structure, remove visor 14 and attempt to wipe the visor clean of the condensed vapor. Such a procedure is disadvantageous because it reduces the number of persons available for fighting the fire. Furthermore, it is dangerous for firefighters in the structure to move about the structure with a fogged, vision obscuring visor. While it might seem that the condensed vapor on the interior surface of visor 14 would be removed in response to the compressed air from tank 16 flowing across the visor on its way toward firefighter 11, it has been found, through actual experience, that this is not the case, probably because air flowing through orifice 9 is sucked by the nose and mouth of firefighter 11 and does not flow over the interior surface of visor 14. The problem has also not been solved by deflecting vapor from the nose and/or mouth of the user toward orifice 9 with a nose cup.

Figure 8:
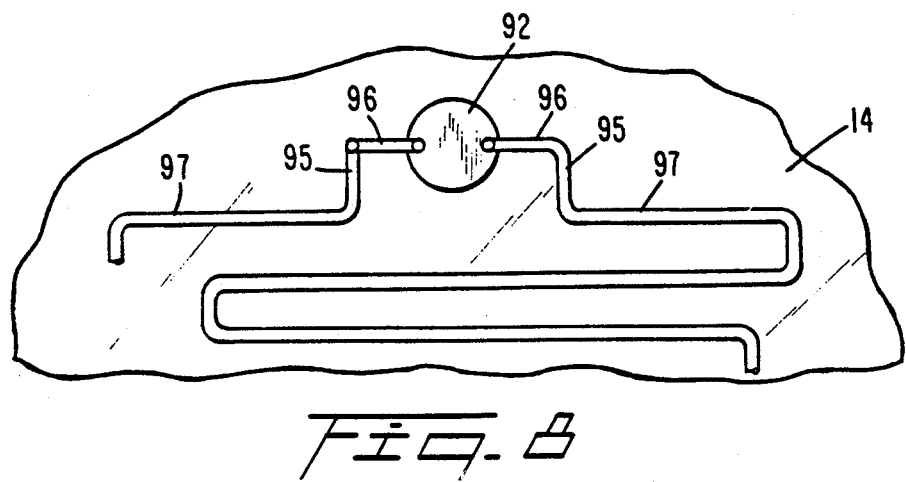
FIG. 8 is a partial view of another embodiment of a visor wherein the visor carries a heating coil and other.

In accordance with one embodiment of the present invention, the condensed vapor on the interior and exterior surfaces of visor 14 is removed by heating the portion of the visor in front of the eyes of firefighter 11. Heat is applied to the portion of visor 14 in front of the eyes of firefighter 11 by supplying electric current to heating coil 21, preferably a metal film coated or deposited on the interior surface of visor 14. Heating coil 21 is dimensioned so that it has a substantial resistance to electric current and is preferably shaped as plural horizontally extending straight lines connected together at the ends thereof by vertically extending straight lines, as disclosed in my previously mentioned U.S. patent and as illustrated in FIG. 8.

Heating coil 21 can be deposited on the interior surface of visor 14 by painting or pad printing a layer of copper covered by a silver layer on the curved visor interior surface. Alternatively, coil 21 is formed by applying a silver silk screening ink through a silk screening mask to a flat blank sheet formed of an organic compound, preferably cellulose diacetate. The ink on the sheet is then heated with an air jet drier for about 20 seconds in the range of 120° to 150° F. The flat blank with the dried ink is then curved into shape and cured so the coil is on the interior surface of visor 14, i.e., the surface having the greatest curvature. To these ends the flat sheet carrying the dried silk screening ink is allowed to cool to room temperature and is then placed in an oven on a drape and/or vacuum form so the sheet surface on which the silk screened ink is located abuts against a drape form and/or a form having apertures through which a vacuum is drawn. The flat sheet is inserted into the oven while the sheet and oven are at room temperature. The oven thermostat is then raised to 325° F., causing the oven temperature to rise quickly to 325° F. The sheet stays in the 325° F. oven for 20 minutes and then removed from the hot oven. In the oven the sheet is curved to the desired shape while being cured.

It has been found that these parameters are important and that some of the parameters are essential in obtaining a visor having the desired shape and transparency, in combination with a silk screened heating coil 21. They are also important or essential for continuity (thickness and width) of silk screened coil 21 to achieve the necessary resistance and continuity along the length of the coil for proper heating of the visor. If the temperature of the flat blank sheet during the drying operation is less than 120° F. the ink drying time is excessive for a commercial manufacturing process. If the blank is at a temperature greater than 150° F. and the drying duration exceeds 20 seconds the amount of heat applied to the sheet causes the organic material thereof to set, resulting in distorted visual properties of the visor after the curing operation. If the curing temperature is appreciably less than 325° F. or curing is for less than about 20 minutes the sheet cannot be bent into shape. If the curing temperature appreciably exceeds 325° F. or curing is for more than about 20 minutes, excessive heat is applied to visor 14 causing the silk screening ink to run on the visor or form to adversely affect electrical properties of coil 21 and reduce the transparency and/or structural integrity.

By bending the blank so the silk screening ink is on the interior surface of visor 14, i.e., the surface having the greater curvature and an area slightly less than that of the flat blank, the silk screening ink is compressed on itself to more positively assure continuity of coil 21. Applying the silk screening ink to the surface of the blank that becomes the visor exterior surface, i.e., the surface of visor 14 having the lower curvature, has been experimentally found to cause adverse effects because the ink has a tendency to break as the area of the ink bearing surface increases during forming. If the silk screening process is employed it is important that the steps be performed as stated to provide proper adherence and geometry, including continuity of the dried silk screening ink, and to preserve the structural integrity and transparency of visor 14.

Figure 2:
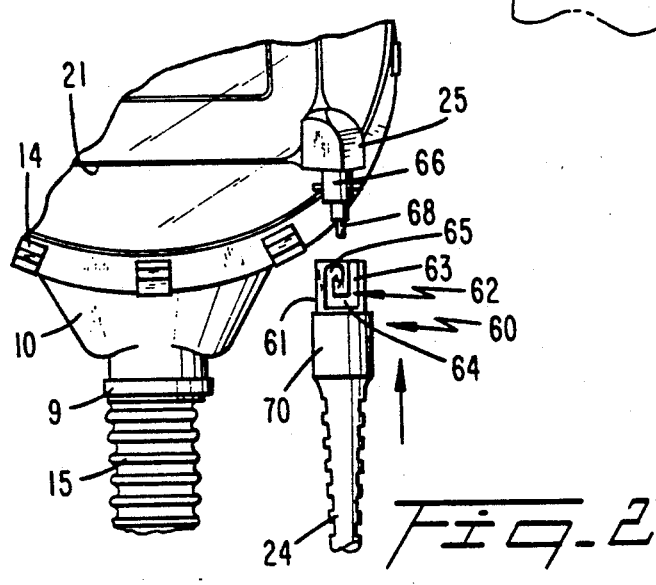
FIG. 2 is a detailed view of a female connector on a lead and a mating part of a male connector on the visor as well as a portion of the visor and face mask of the SCBA device illustrated in FIG. 1.

It has also been found that the high resistivity of silk screened coil 21 causes hot spots of the corners of the coil where the horizontal and vertical stripes intersect, if the corners are square. Further hot spots develop at the intersections of connector with silk screened coil 21. The reduced thickness of the silk screened layer relative to the thickness of the painted or pad printed layers causes the silk screened coil to be more resistive than the other types of layers, resulting in the hot spots which can cause the melting of visor 14. To overcome this hot spot problem, silk screened coil 21 is preferably rounded at the corners thereof where the horizontal and vertical stripes intersect as illustrated in FIGS. 1, 2 and 8. Further, the width of the coil is increased in the region where the coil engages and is in close proximity to connector 25, as illustrated in FIG. 2. In all other regions, coil 21 has uniform width and thickness dimensions.

Electric current is supplied to heating coil 21 from a battery pack including rechargeable battery 22 that is carried in metal housing 23, shaped as a right parallelepiped. Battery 22 is preferably a 12 volt, 1.5 ampere hour rechargeable gel cell, as available from Globe Battery Division of Johnson Controls, Inc. The gel cell type battery is advantageous because it can withstand the intense heat to which it may be exposed, without exploding. A rechargeable lead battery is very likely to explode in the firefighting application.

Current from battery 22 is supplied to heating coil 21 by way of helical coaxial electrical cable 24, fixedly mounted on gas line 20 between regulator 17 and adjustable valve 19, carried by tank 16. Cable 24 extends along line 20 until just before the line is connected to regulator 17, where the cable leaves line 20 and extends freely to connector 25 on visor 14. Cable 24 is helical and hose 15 is corrugated so they do not impede the movement of firefighter 11.

As illustrated in FIGS. 4 and 5, housing 23 for battery 22 is fixedly mounted on metal strap 31 that extends about and is fixedly secured to tank 16 by clip 32. Metal strap 31 is secured to tank 16 to enable the tank to be carried by harness 18 that goes over the shoulders of firefighter 11, as well known to those familiar with SCBA. To prevent damage to rechargeable battery 22 due to excessive ambient heat, which can cause the battery to discharge at an excessively high rate, all six interior walls of housing 23 are lined with thermal, dielectric insulating pads 34, preferably constructed of STYROFOAM. Pads 34 have exterior faces bonded to corresponding interior faces of housing 23. The corresponding exterior faces of pads 34 and the interior faces of housing 23 have the same shape and about the same exterior dimensions.

Clip 32 is fixedly mounted on housing 23 so that relatively short, transverse housing wall 33 is generally horizontal. On wall 33 are fixedly mounted female coaxial electric connector 134, green light emitting diode 35, red light emitting diode 135 and on-off pivoting switch 36. Electric leads of connector 134, diodes 35 and 135, as well as switch 36, extend through apertures in wall 33 and are connected together on the inside face of wall 33 and to leads 37 from battery 22, which extend through small openings in the pad 34 abutting against wall 33. Connector 134 receives male coaxial connector 61 at one end of the cable or a male connector of a battery charger. (To show the physical arrangement of the leads connecting connector 134, lamp 35 and switch 36 and leads 37, the pad 34 abutting against wall 33 is illustrated in FIG. 5 as being partially broken away.)

To provide access to battery 22 and enable the battery to be removed for replacement purposes, wall 38 of housing 23 is connected by hinge 39 to wall 41 of the container and by screws 42 which engage threaded bores 43 in wall 44. To provide a tight, waterproof seal between top wall 38 and the remaining walls of container 23, rubberized gasket 45 extends upwardly from the sidewalls of container 23 for engagement with the peripheral portion of the inside face of top wall 38.

Figure 6:
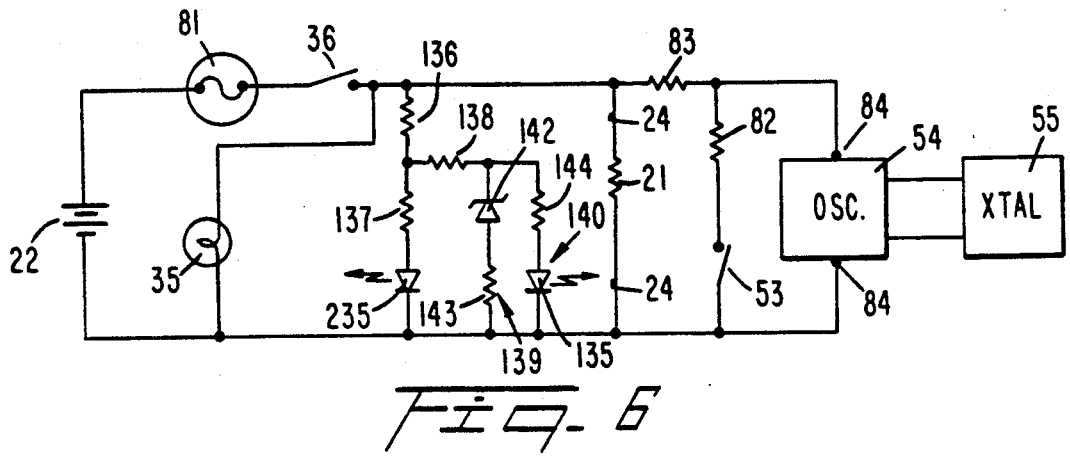
FIG. 6 is an electric circuit diagram including a heater coil illustrated in FIGS. 1 and 2, as well as for detecting excessive temperature and signaling same.

Battery housing 23 also carries an electric circuit, FIG. 6, for detecting excessively high temperatures, dangerous to firefighter 11, and for providing the firefighter with an aural warning of such excessive temperature. The circuit is powered by battery 22 while switch 36 is pivoted to the closed state. To these ends, mounted on the exterior of wall 33 is sealed temperature detector 51, including a membrane 52 behind which is located bi-metal contacts 53; the membrane enables contacts 53 to be at about the same temperature as the environment where firefighter 11 is located. Bi-metal contacts 53 are normally closed because such an arrangement is more reliable than normally opened contacts in the presence of a dirty environment as encountered in burning structures and mines. Contacts 53 have a hysteresis or dead band characteristic so that they are closed for temperatures rising from room temperature or below to 125° F. At 125° F., contacts 53 open circuit and remain open circuited until the temperature to which they are exposed drops to less than 105° F., at which temperature the contacts again close.

While contacts 53 are open, oscillator circuit 54 mounted on the interior face of wall 33, is activated to supply a pulsed audio frequency carrier signal to piezoelectric crystal 55, mounted on top wall 38 of housing 23. Typically, the pulses occur about once every 10 seconds, have a duty cycle of about 10% and a carrier frequency of about 1 kHz.

Crystal 55 is positioned on wall 38 behind metal grill screen 56, which fills an opening on wall 38. When oscillator 54 is activated in response to contacts 53 being open circuited, the oscillator supplies a periodic electric pulsed audio frequency signal to crystal 55. Crystal 55 converts or transduces the electric signal supplied to it by oscillator 54 into an acoustic or aural signal having sufficient intensity to be heard by firefighter 11. Thereby, firefighter 11 is provided with an aural warning that he should leave the burning structure because it is excessively hot and may cause him damage. The aural signal can also be used to advise the presence of a disabled firefighter.

When switch 36 is activated to the on position and male connector 61 at the end of cable 24 is connected into female connector 134 on housing 23, current is supplied by battery 22 via cable 24 to heating coil 21. The connection from cable 24 to heating coil 21 is via connector 25, fixedly mounted on visor 14 so that it is electrically connected to opposite terminals of coil 21, as disclosed in my aforementioned patent. Connector 25, however, is modified so that one end of cable 24 can be selectively inserted into and removed from the connector. The arrangement is such that cable 24 is not pulled from connector 25 as a result of the free portion of the cable, between line 20 and connector 25, having debris fall on it. Cable 24 can be removed from connector 25 only by simultaneous pushing and twisting of the end of the cable which fits into connector 25, operations easily performed by firefighter 11 when he wants to remove face shield 10 or visor 14 from face shield 10.

To these ends, as illustrated in FIGS. 2 and 3 at the end of cable 24 which is inserted into connector 25 is connector 60 including metal sleeve 61, electrically connected to a coaxial shielded lead (not shown) of cable 24. Sleeve 61 includes a pair of diametrically opposed slots 62, each having a longitudinally extending segment 63, an arcuately extending segment 64 and an ear 65 which extends from segment 64 toward the top edge of sleeve 61 where longitudinal slotted segment 63 begins. Slot 62 engages radially extending metal pin 66 on dielectric stub shaft 67 of connector 25; shaft 67 extends downwardly from the remainder of connector 25. Pins 66 are connected via connector 25 to one terminal of heating coil 21 via lead wire 73 in connector 25. The remaining terminal of heating coil 21 is connected via lead wire 74, contact 75 and metal compression spring 76 in connector 25 to longitudinally extending metal pin 68, mounted in and coaxial with stub shaft 67. Compression spring 76 biases pin 68 inside of stub shaft 67 so that pin 68 normally extends beyond the end of the stub shaft by a distance equal to the distance between the top edge of sleeve 61 and the intersection of the sleeve with dielectric case 70 from which the sleeve extends. Centrally located in cavity 71 of case 70 is contact 69 that is electrically connected to the center conductor of cable 24 and electrically insulate from sleeve 61.

In operation, connector 60 is inserted on connector 25 by placing sleeve 61, having a diameter slightly in excess of the diameter of stub shaft 67, about the stub shaft so that slot portions 63 are aligned with pins 66. Connector 60 is then pushed into stub shaft 67 until pins 66 are in proximity to the bottom of slot portion 63, i.e., the portions of slot 62 farthest away from the top edge of sleeve 61. Pin 68 now engages contact 69 and the pin is in the fully retracted position. Connector 60 is then turned so that slot portions 64 turn about pins 66 until the pins 62 are aligned with ears 65, at which time connector 60 is released. The spring bias exerted against pin 68, thence against contact 69, causes pins 66 to seat against the edges of ears 65 closest to the top edge of sleeve 61. Thereby, longitudinally extending pin 68 is urged by the compression spring against contact 69 to establish positive electrical and mechanical contact between pins 66 and 68 and the shield and the interior lead of cable 24.

FIG. 6 is an electric circuit diagram of the electrical components included in housing 23 and connected to heating coil 21. Battery 22 is connected to the remainder of the circuit through fuse 81, mounted on the interior face of wall 33. Fuse 81 is connected to switch 36 which, when activated into the "on" position, causes current to flow from battery 22 through lamp 35 to energize the lamp. When cable 24 is connected to connectors 25 and 134, current flows from battery 22 to, fuse 81, switch 36 and cable 24 to heating coil 21.

Connected in shunt with lamp 35 is series resistor 83 and a first branch including the series combination of resistor 82 and normally closed bi-metal contacts 53, as well as a second branch, in parallel with the first branch; the second branch includes power supply terminals 84 of oscillator 54. Resistors 83 and 82 have a sufficiently large value to prevent excessive current drain from battery 22 while contacts 22 are closed. In response to temperature sensing contacts 53 being in the normally closed state, oscillator 54 is de-energized because the voltage across terminals 84 is insufficient to power oscillator 54. In response to contact 53 being open-circuited because of excessive temperature being detected, the voltage across terminals 84 increases, causing oscillator 54 to become activated to supply a pulsed carrier signal to piezoelectric crystal 55.

Green light emitting diode (LED) 235 and red LED 135 are connected in circuit with battery 22 to signal to the firefighter whether battery 22 has sufficient energy to defog mask 14 for a sufficient time to warrant insertion of a new air tank 16. For air tanks having a 20 minute capability, as is typically employed, the voltage of battery 22 must exceed 8.5 volts for the type of battery previously mentioned. If the voltage of battery 22 is greater than 8.5 volts, associated with the battery having sufficient energy to power coil 21 for more than 20 minutes with enough current to prevent fogging of mask 14, green LED 235 is energized. If the voltage of battery 22 is less than 8.5 volts, associated with the battery having insufficient energy to power coil 21 for more than 20 minutes with enough current to prevent fogging of mask 14, red LED is energized.

To these ends, LEDs 235 and 135 are connected in separate branch circuit to battery 22 via series resistor 136. The branch circuit including LED 235 includes resistor 137, connected in series with the LED. One terminal of resistor 138 is connected to a common terminal of resistors 136 and 137; the other terminal of resistor 138 is connected to parallel branch circuits 139 and 140, respectively including zener diode 142 and LED 135. Circuits 139 and 140 respectively include current limiting resistors 143 and 144. The characteristics of diodes 235, 135 and 142 and the values of diodes 136–138, 143 and 144 are selected for the type of battery 22 and the characteristics of coil 21 such that diode 235 is energized in response to the voltage of battery exceeding 8.5 volts. For voltages of battery 22 above 8.5 volts, zener diode 142 is activated to a conducting state causing the voltage across and/or the current through diode 135 to be low enough to prevent activation of LED 135. The values of diodes 136–138 are such that the low impedance of diode 142 does not affect energization of diode 235. For voltages of battery 22 less than 8.5 volts, LED 235 is de-energized and zener diode 142 is switched to a nonconducting state. The voltage applied to red LED 135 is then sufficient to activate the red LED. The firefighter is thereby provided with a convenient indication as to whether or not battery 22 must be replaced or recharged at the time a new air bottle is put into service.

Figure 7:
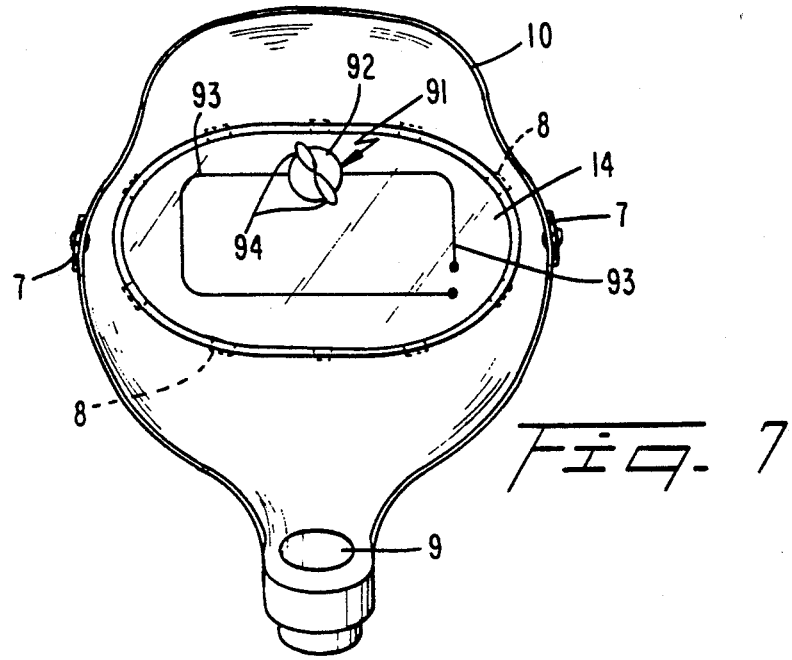
FIG. 7 is a back view of a second embodiment of a face mask in accordance with the invention wherein a fan draws air from a gas tank carried by the user across the visor.

A supplemental or alternative structure for removing condensate from the interior surface of visor 14 is to fixedly position fan 91 on the interior surface of the visor just below the top edge of the visor half way between the opposite side edges of the visor as illustrated in FIG. 7. Low voltage DC motor 92 of fan 91 is electrically connected to be energized by battery 22 via cable 24 and the terminals on visor 14 by low resistance leads 93 formed on the visor interior surface in a manner similar to that described for coil 21. Leads 93 extend about the periphery of visor 21 so they do not obstruct the vision of the firefighter and have a considerably greater thickness and width, but total shorter length than coil 21 so that almost the full voltage of battery 21 is delivered to motor 92 with minimum current dissipation. Alternatively, motor 92 has a very low voltage rating and the armature coil thereof is connected in series with coil 21 by a pair of leads 95 deposited on visor 14 and connected via wires 96 to upper most lead 97 of coil 21, as illustrated in FIG. 8.

Blades 94 of fan 91 suck dry air from tank 16 flowing through orifice 9 across the interior surface of visor 14 prior to the air being inhaled by firefighter 11 to remove the condensate from the visor interior surface and provide a curtain of dry air that tends to prevent the flow of vapor from the face of the firefighter to the visor interior surface. After the air flowing through orifice 9 that has been drawn upwardly across visor 14 by blades 94 has passed through the blades it is inhaled by firefighter 11.

While there have been described and illustrated several specific embodiments of the invention, it will be clear that variations in the details of the embodiments specifically illustrated and described may be made without departing from the true spirit and scope of the invention as defined in the appended claims.

I claim:

1. A method of forming an optically transparent, curved visor of a type to be used with a helmet, the visor being formed to have an electric heater thereon, comprising the steps of: applying metal silk screen ink through a silk screen form onto a flat optically transparent organic sheet; drying the ink on the flat sheet such that the optical properties of the transparent sheet are not substantially affected; placing the flat sheet with the dried silk screen ink thereon into an oven on a form curved to the approximate final shape of the visor; while the flat sheet is on the form in the oven, raising the temperature of the flat sheet so the flat sheet becomes plastic while exerting a force on the flat sheet so a surface of the sheet conforms approximately to the shape of the form, the temperature of the oven and the length of time the sheet is at the raised temperature being such that (a) mechanical and electrical characteristics of the silk screening ink on the sheet are not substantially affected and (b) the optical characteristics of the sheet are not substantially affected.

2. The method of claim 1 wherein the ink is dried on the flat sheet by applying a jet of gas having a temperature above room temperature to the ink on the flat sheet, the jet of gas having a temperature and being applied for a length of time such that the optical transparency properties of the sheet are not substantially affected.

3. The method of claim 2 wherein the sheet is formed of cellulose diacetate and has a temperature of about 120° F. to 150° F. while the jet of gas is applied thereto and the get of gas is applied for about 20 seconds to the ink while the ink is wet.

4. The method of claim 3 wherein the oven is heated so the temperature of the sheet is about 325° F. for about 20 minutes.

5. The method of claim 4 wherein the force is exerted by applying a vacuum to the sheet through the form.

6. The method of claim 5 wherein the force is exerted by applying a drape to the sheet.

7. The method of claim 4 wherein the force is exerted by applying a drape to the sheet.

8. The method of claim 1 wherein the sheet is cellulose diacetate and the oven is heated so the temperature of the sheet is about 325° F. for about 20 minutes.

9. The method of claim 8 wherein the force is exerted by applying a vacuum to the sheet through the form.

10. The method of claim 9 wherein the force is exerted by applying a drape to the sheet.

11. The method of claim 8 wherein the force is exerted by applying a drape to the sheet.

12. The method of claim 1 wherein the force is exerted by applying a drape to the sheet.

13. The method of claim 1 wherein the force is exerted by applying a vacuum to the sheet through the form.

14. The method of claim 13 wherein the force is exerted by applying a drape to the sheet.

15. The method of claim 1 wherein the surface to which the silk screen ink is applied is the curved surface of the formed visor having the greatest curvature.

16. A method of forming an optically transparent, curved visor of a type to be used with a helmet, the visor being formed to have an electric heater thereon, comprising the steps of: applying metal silk screen ink through a silk screen form onto a flat optically transparent organic sheet; drying the ink on the flat sheet such that the optical properties of the transparent sheet are not substantially affected; placing the flat sheet with the dried silk screen ink thereon into an oven on a form curved to the approximate final shape of the visor; while the flat sheet is on the form in the oven, raising the temperature of the flat sheet so the flat sheet becomes plastic while exerting a force on the flat sheet so a surface of the sheet conforms approximately to the shape of the form, the temperature of the oven and the length of time the sheet is at the raised temperature being such that the silk screening ink does not run on the sheet and does not cause the optical properties of the sheet to become distorted.

17. The method of claim 16 wherein the surface to which the silk screen ink is applied is the curved surface of the formed visor having the greatest curvature.

18. A method of forming a heating coil on a curved optically transparent organic sheet initially formed as a flat transparent sheet comprising applying metal silk screen ink through a silk screen form onto the flat optically transparent organic sheet; drying the ink on the flat sheet such that the optical properties of the transparent sheet are not substantially affected; placing the flat sheet with the dried silk screen ink thereon into an oven on a form curved to the approximate final shape of the visor; while the flat sheet is on the form in the oven, raising the temperature of the flat sheet so the flat sheet becomes plastic while exerting a force on the flat sheet so a surface of the sheet conforms approximately to the shape of the form, the temperature of the oven and the length of time the sheet is at the raised temperature being such that (a) mechanical and electrical characteristics of the silk screening ink on the sheet are not substantially affected and (b) the optical characteristics of the sheet are not substantially affected, the surface to which the silk screen ink is applied being the curved surface of the formed visor having the greatest curvature.

* * * * *